(12) United States Patent
Wei (10) Patent No.: US 8,241,257 B2
(45) Date of Patent: Aug. 14, 2012

(54) PEN NEEDLE ASSEMBLY

(75) Inventor: Min Wei, Morris Plains, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 12/863,093

(22) PCT Filed: Jan. 13, 2009

(86) PCT No.: PCT/US2009/030798
§ 371 (c)(1),
(2), (4) Date: Jan. 5, 2011

(87) PCT Pub. No.: WO2009/091707
PCT Pub. Date: Jul. 23, 2009

(65) Prior Publication Data
US 2011/0106016 A1    May 5, 2011

Related U.S. Application Data

(60) Provisional application No. 61/011,136, filed on Jan. 15, 2008.

(51) Int. Cl.
*A61M 5/00* (2006.01)
*A61M 5/31* (2006.01)
*A61M 5/24* (2006.01)
*A61M 5/28* (2006.01)

(52) U.S. Cl. ........ 604/242; 604/200; 604/201; 604/206; 604/232; 604/240; 604/244

(58) Field of Classification Search .................. 604/200, 604/201, 206, 240, 241, 242, 243, 181, 187, 604/218, 232, 244
See application file for complete search history.

(56) References Cited

U.S. PATENT DOCUMENTS

| 2,828,742 | A | * | 4/1958 | Ashkenaz | 604/193 |
| 4,449,539 | A | * | 5/1984 | Sarstedt | 600/577 |
| 4,731,059 | A | | 3/1988 | Wanderer et al. | |
| 5,505,694 | A | * | 4/1996 | Hubbard et al. | 604/512 |
| 5,829,589 | A | | 11/1998 | Nguyen et al. | |
| 5,873,462 | A | | 2/1999 | Nguyen et al. | |
| 5,931,817 | A | | 8/1999 | Nguyen et al. | |
| 5,941,857 | A | | 8/1999 | Nguyen et al. | |

(Continued)

FOREIGN PATENT DOCUMENTS
EP    0 704 225 A2    4/1996
(Continued)

*Primary Examiner* — Kevin C. Sirmons
*Assistant Examiner* — Shefali Patel
(74) *Attorney, Agent, or Firm* — Hoffmann & Baron, LLP (57) ABSTRACT

A pen needle assembly is provided herein for use with a medical injector containing an injector body and a reservoir sealed by a septum encased in the injector body. The pen needle assembly includes a hub and a needle fixed to the hub. The hub is formed to be telescopingly mounted onto a distal end of the injector body using a track that accommodates a guide key. When mounting the hub of the pen needle assembly onto the injector body, a first portion of the track is configured to receive the guide key and to guide the guide key in a straight line across sufficient distance to permit a proximal end of the needle to fully pierce through the septum, without rotation of the needle. A second portion of the track is configured to permit the pen needle assembly to be turned with the proximal end of the needle being located proximally of the septum.

13 Claims, 14 Drawing Sheets

U.S. PATENT DOCUMENTS

| | | |
|---|---|---|
| 5,944,700 A | 8/1999 | Nguyen et al. |
| 6,017,331 A | 1/2000 | Watts et al. |
| 6,120,478 A * | 9/2000 | Moore et al. ............ 604/110 |
| 6,146,361 A | 11/2000 | DiBiasi |
| 6,200,296 B1 | 3/2001 | Dibiasi et al. |
| 6,595,960 B2 | 7/2003 | West et al. |
| 7,314,464 B2 | 1/2008 | Giambattista et al. |
| 7,462,168 B2 | 12/2008 | Stonehouse et al. |
| 7,462,169 B2 | 12/2008 | Follman et al. |
| 7,540,858 B2 | 6/2009 | DiBiasi |
| 2001/0014792 A1 | 8/2001 | West et al. |
| 2004/0147855 A1 | 7/2004 | Marsden |
| 2008/0177235 A1 | 7/2008 | DiBiasi |
| 2009/0069753 A1 | 3/2009 | Ruan et al. |
| 2011/0022001 A1 | 1/2011 | Wei |

FOREIGN PATENT DOCUMENTS

| | | |
|---|---|---|
| FR | 2 884 723 B1 | 10/2006 |
| GB | 836278 | 6/1960 |
| WO | 96/11028 A1 | 4/1996 |
| WO | 01/91837 A1 | 12/2001 |
| WO | 2006/103074 A1 | 10/2006 |

* cited by examiner

PEN NEEDLE ASSEMBLY

CROSS-REFERENCE TO RELATED APPLICATIONS

The present application is the U.S. national stage application of International Application PCT/US2009/030798, filed Jan. 13, 2009, which international application was published on Jul. 23, 2009, as International Publication WO 2009/091707. The International Application claims the benefit of U.S. Provisional Patent Application 61/011,136, filed Jan. 15, 2008.

FIELD OF THE INVENTION

This invention relates to pen needle assemblies for pen injectors.

BACKGROUND OF THE INVENTION

Pen needle assemblies are known in the prior art for use with pen injectors. Pen needle assemblies are individually provided for a pen injector and include a hub attached to a needle. Typically, the assemblies are formed to be removably mounted to the pen injector and disposed after use. With multiple-dose pen injectors, a plurality of pen needle assemblies are mounted and removed from the injector.

The needles used with pen needle assemblies are of limited length. The needles must have sufficient proximal length to pierce a septum of a medicament reservoir and have sufficient distal length to be inserted into a patient for a medical injection. Prior art pen assembly designs have been found to cause "tenting" of a drug reservoir septum when the proximal part of the needle does not sufficiently pass through the septum. As such, the septum may not be fully penetrated or the septum is distorted resulting in possible incorrect drug administration. An overly-sized proximal portion of the needle may be used to avoid "tenting." However, an excessively long needle in the proximal direction may not efficiently convey medicament from low levels in a drug reservoir.

Additionally, pen needle assemblies are typically attached to the pen injector by rotating the needle, while inserting the needle into the septum of a medicament reservoir. The combined rotating and traversing motion of the needle may cause coring of the septum. The septum is formed to be resealable upon removable of the pen needle assembly. With a cored septum, a portion of the septum may not be resealable, resulting in the need to dispose of the reservoir.

SUMMARY OF THE INVENTION

A pen needle assembly is provided herein for use with a medical injector. The pen needle assembly includes a hub and a needle fixed to the hub. The needle has a distal end, formed for insertion into a patient, and a proximal end. The medical injector further includes an injector body being tubular in shape with a distal end and a proximal end and a reservoir sealed by a septum encased in the injector body. The hub is formed to be telescopingly mounted onto the distal end of the injector body using a track that accommodates a guide key. When mounting the pen needle assembly onto the injector body, a first portion of the track is configured to receive the guide key and to guide the guide key in a straight line across sufficient distance to permit the proximal end of the needle to fully pierce through the septum, without rotation of the needle and with the proximal end of the needle being guided to a location proximal of the septum. A second portion of the track is configured to permit the pen needle assembly to be turned with the guide key being received in the second portion of the track with the proximal end of the needle being located proximally of the septum. Advantageously, with the arrangement of the subject invention, coring of a drug cartridge septum may be generally avoided with repeated mounting of pen needle assemblies onto the medical injector.

These and other features of the invention will be better understood through a study of the following detailed description and accompanying drawings.

DETAILED DESCRIPTION OF THE DRAWINGS

With reference to the Figures, a medical injector 10 is provided herein. The medical injector 10 may be of various injector configurations. The present invention is well-suited with the medical injector 10 being a pen injector.

Figure 1:
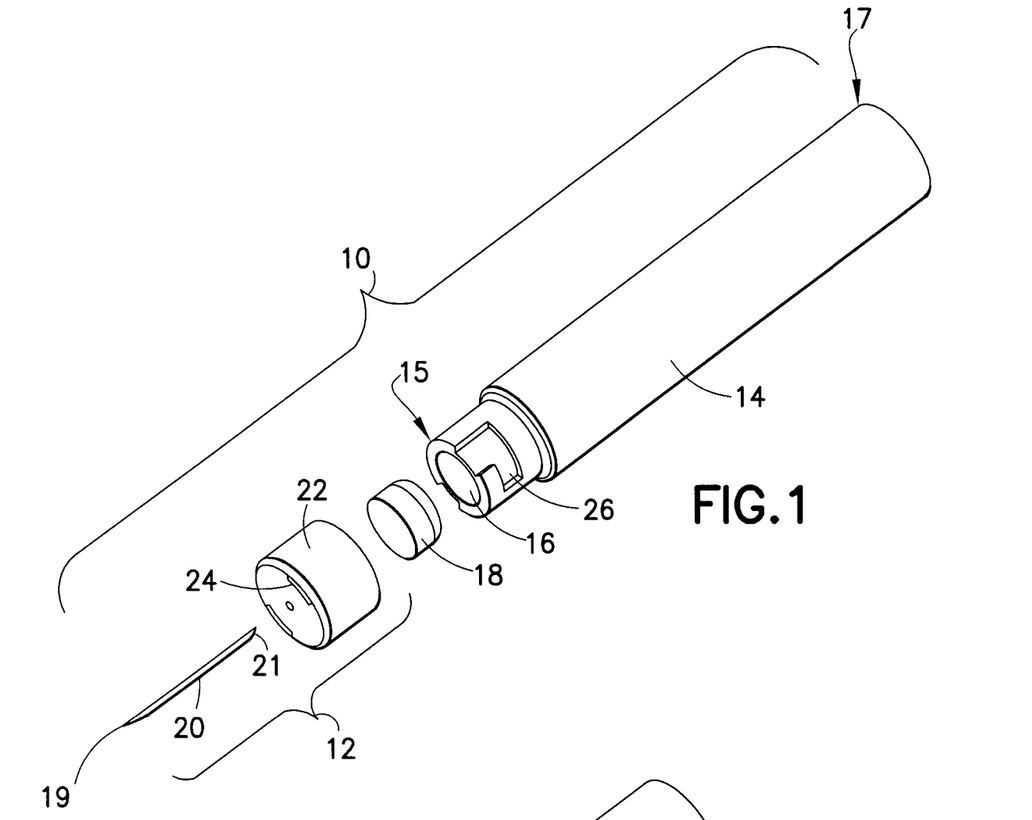
FIG. 1 depicts an exploded view of a medical injector formed in accordance with the present invention.
Figure 2:
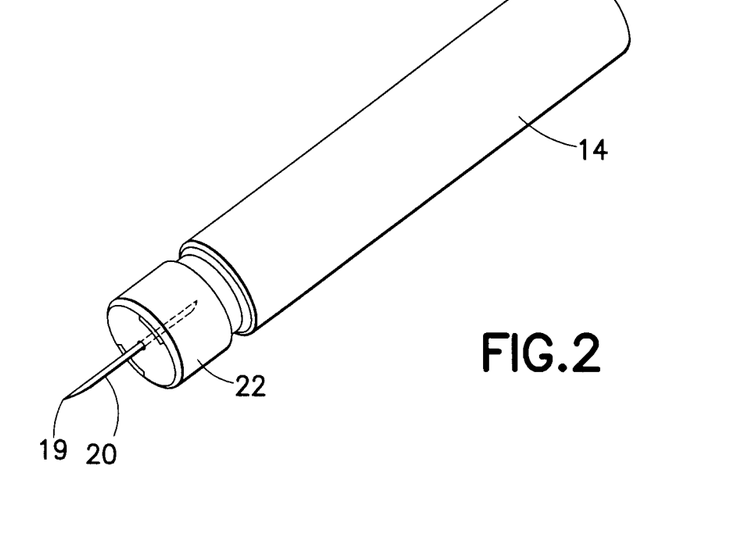
FIG. 2 depicts an assembled view of a medical injector formed in accordance with the present invention.
Figure 3:
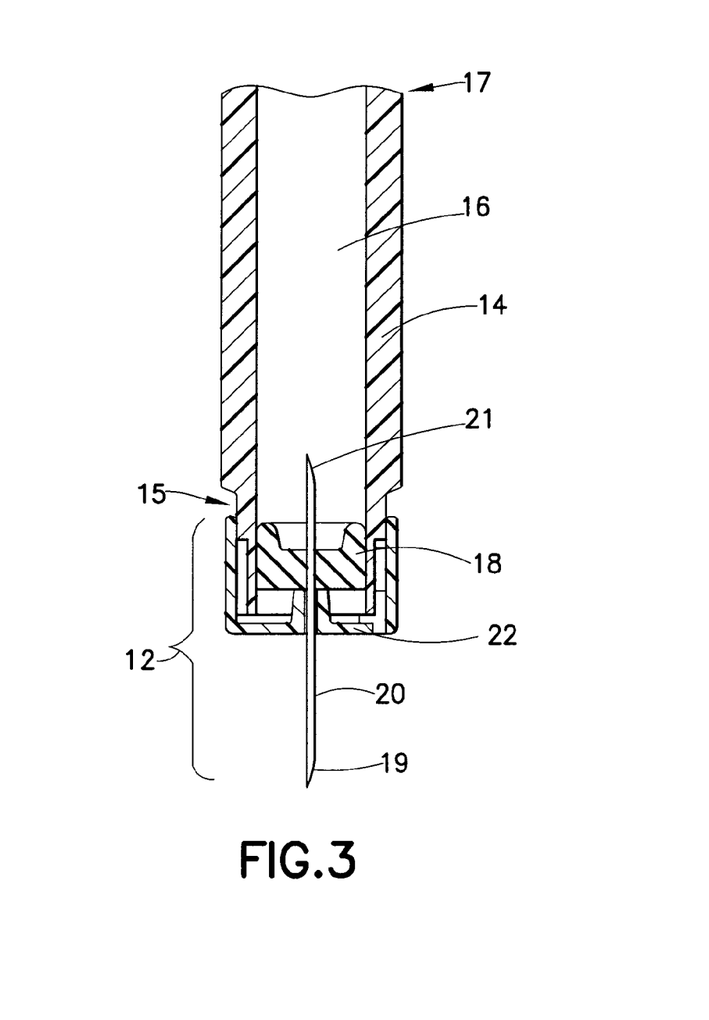
FIG. 3 depicts a partial cross-section of a medical injector of a first embodiment of a pen needle assembly of the present invention.

As shown in FIGS. 1-3, the medical injector 10 generally includes: a pen needle assembly 12; an injector body 14, including a distal end 15 and a proximal end 17; and a reservoir 16 for medicament sealed by a septum 18. The reservoir 16 is encased within the injector body 14 and may be defined by the injector body 14 or defined by a separate component contained within the injector body 14 (e.g., a cartridge).

The pen needle assembly 12 further includes a needle 20 and a hub 22. The needle 20 includes a distal end 19, formed for insertion into a patient, and a proximal end 21. The assembly 12 is configured to guide the needle 20 in a straight line to permit the proximal end 21 of the needle 20 to fully pierce through the septum 18 without rotation of the needle 20. To obtain this configuration, a guide key 24 is provided on one of the hub 22 or the injector body 14 with a track 26 being defined on the other of the hub 22 or the injector body 14. It is preferred that the guide key 24 be formed on the hub 22 and that the track 26 be defined on the injector body 14.

FIG. 3 shows the pen needle assembly 12 attached to the injector body 14 with the needle 20 inserted into the reservoir 16 at a location above the septum 18.

Figure 4:
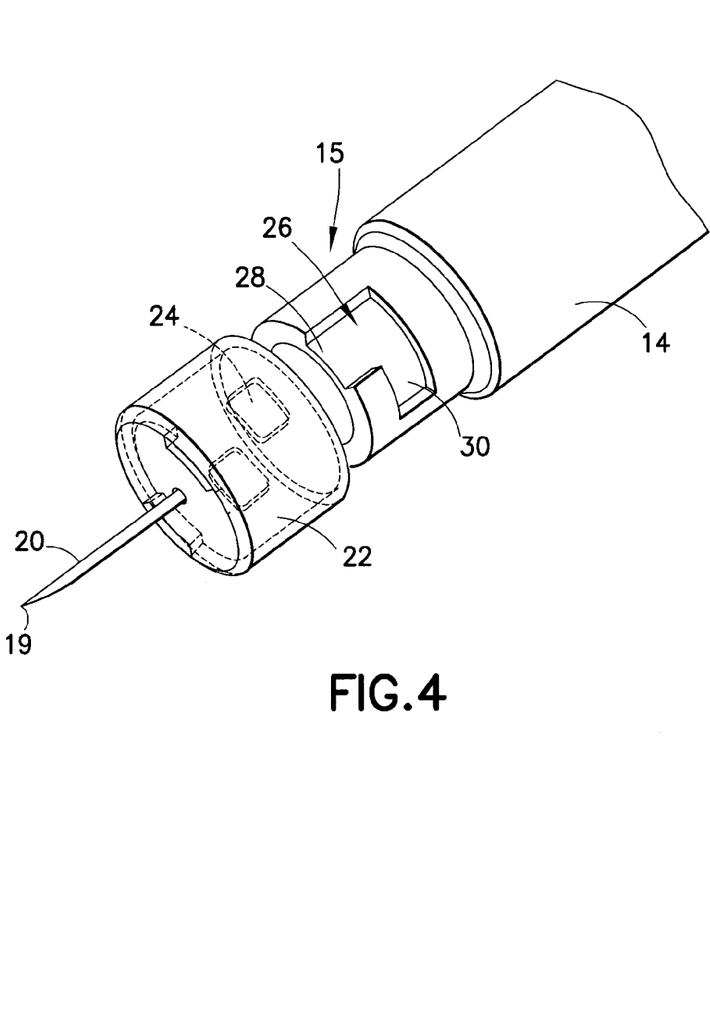
FIGS. 4-6 depict different stages of a pen needle assembly being mounted to an injector body.

The track 26 may be formed with two portions. With reference to FIG. 4, the injector body 14 with the track 26 having two portions is shown on a distal end 15 of the injector body 14. A first portion 28 of the track 26 extends proximally from the distal end 15 of the injector body 14, and a second portion 30 of the track 26 is disposed transversely to the first portion 28.

Figure 20:
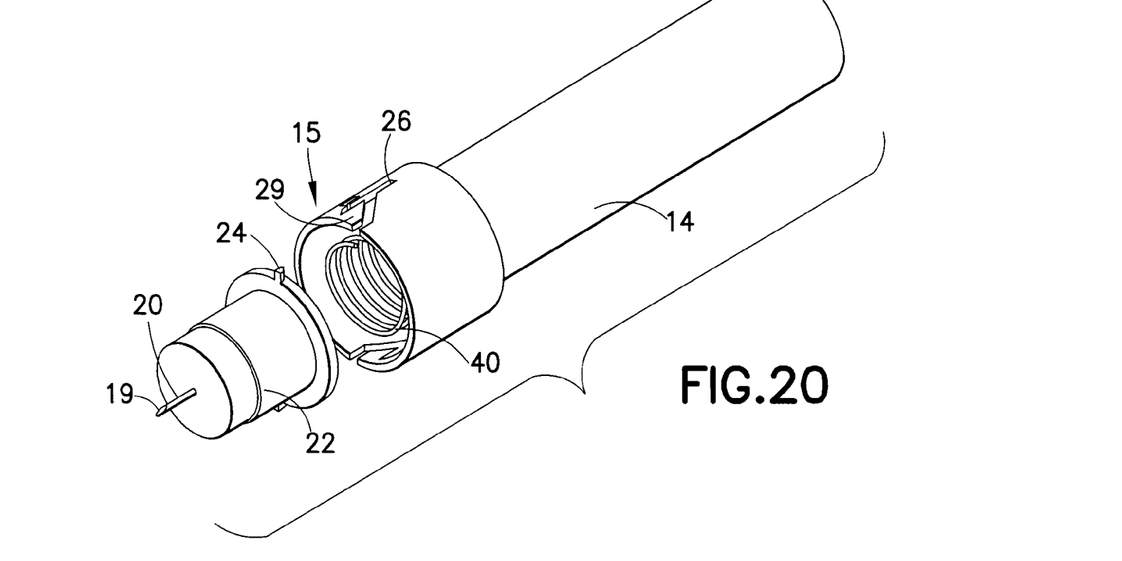

FIG. 4 further shows the pen needle assembly 12 containing the hub 22 with the needle 20 and the guide key 24 along an inner portion of the hub 22. The guide key 24 is a flange of limited length, which may be located on various portions of the hub 22. More particularly, the present invention contemplates the guide key 24 being located on the inner portion of the hub 22, as illustrated in FIG. 4, or on an outer portion of the hub 22, as illustrated in FIG. 20. The injector body 14 of FIG. 4 is configured to enable the guide key 24 to be inserted into the first portion 28 of the track 26 and guided through the second portion 30 of the track 26. As shown in FIG. 4, more than one of the guide keys 24 may be provided, e.g., two, with a corresponding number of tracks 26 being provided. The guide keys 24 are discontinuous and evenly spaced.

Figure 5:
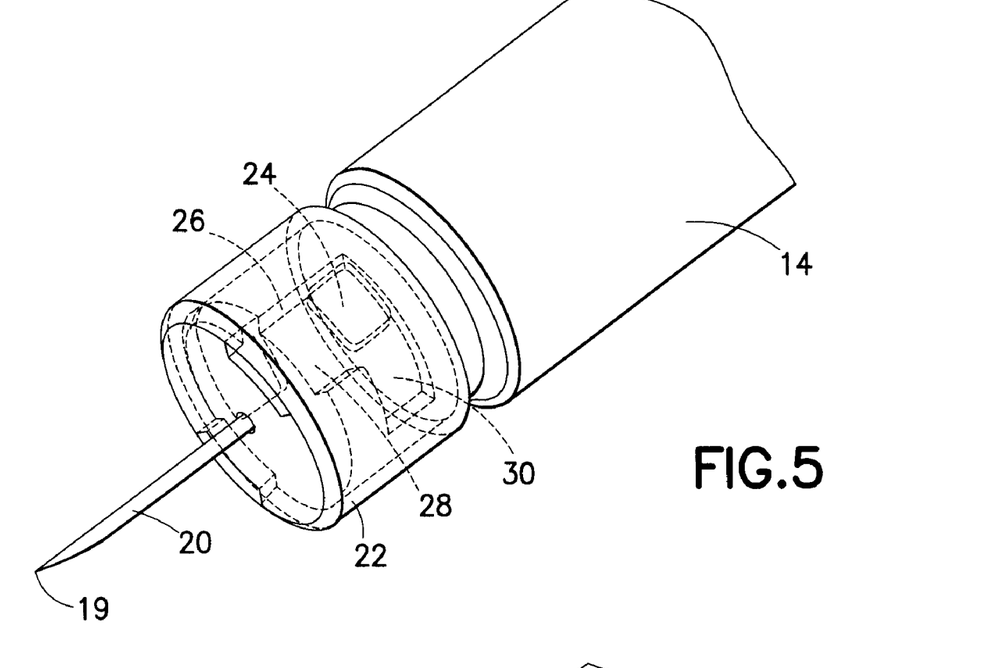
Figure 6:
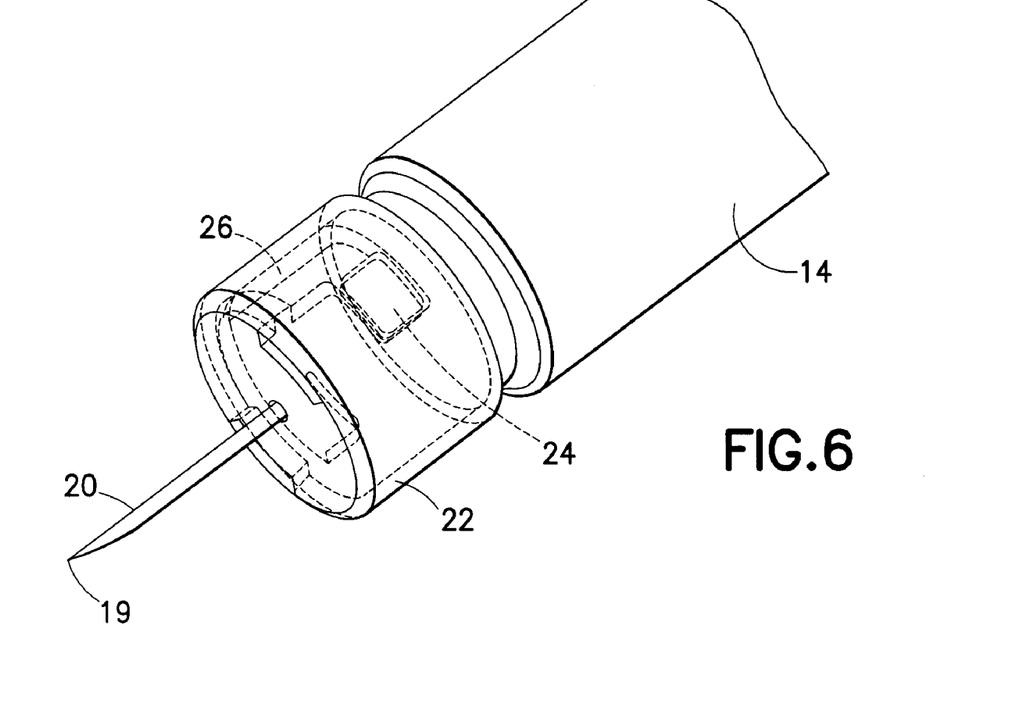

With reference to FIGS. 5-6, during use, the pen needle assembly 12 is first inserted into the injector body 14 with the guide key 24 being accommodated in the first portion 28 of the track 26. As the first portion 28 of the track 26 receives the guide key 24, the pen needle assembly 12 is guided in a straight line across a sufficient distance to permit the proximal end 21 of the needle 20 to fully pierce the septum 18 without rotation of the needle 20. Once the proximal end 21 of the needle 20 is guided a sufficient distance proximal to the septum 18, the guide key 24 is received by the second portion 30 of the track 26. The second portion 30 of the track 26 is configured to permit the pen needle assembly 12 to be turned, while keeping the proximal end 21 of the needle 20 proximal to the septum 18.

Figure 7:
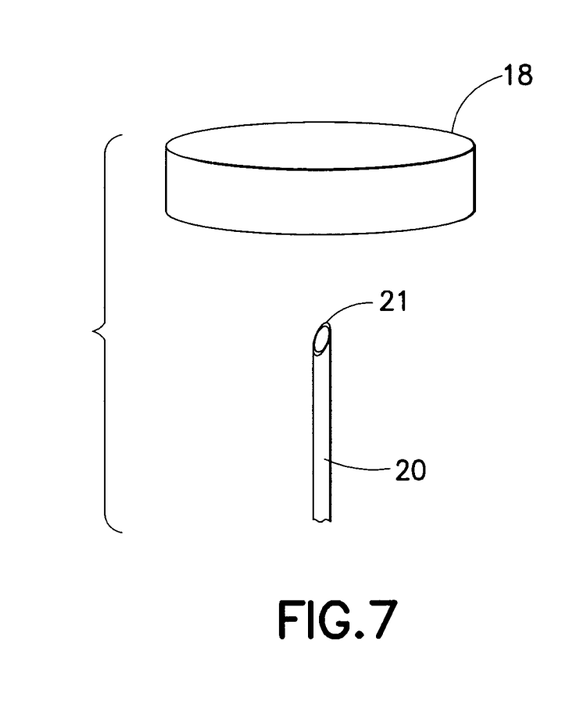
FIGS. 7-9 depict a needle of the pen needle assembly formed in accordance with the subject invention prior to, during, and after piercing the septum.
Figure 8:
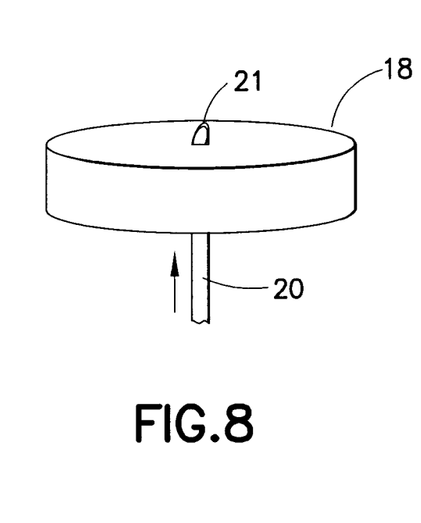
Figure 9:
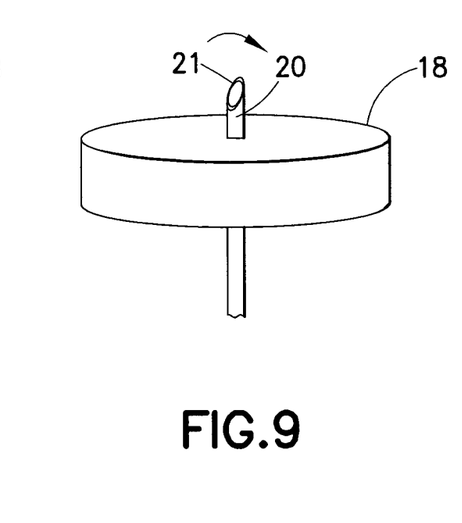

FIGS. 7-9 further illustrate the phases of the needle 20 piercing the septum 18, as the pen needle assembly 12 is mounted onto the injector body 14 (described in FIGS. 5-6). FIG. 7 shows the needle 20 and the septum 18 prior to the pen needle assembly 12 being mounted to the injector body 14. With reference to FIG. 8, when piercing the septum 18, the needle 20 is first guided in a straight line across a sufficient distance to permit the proximal end 21 of the needle 20 to fully pierce the septum 18. Then, after the needle 20 fully pierces the septum 18, the needle 20 is rotated, as shown in FIG. 9. The needle 20 is only rotated after the needle 20 fully pierces the septum 18 to prevent the sharp proximal 21 end of the needle 20 from coring the septum 18.

The pen needle assembly as shown in FIGS. 1-9 may be placed on and off an injector freely.

Figure 10:
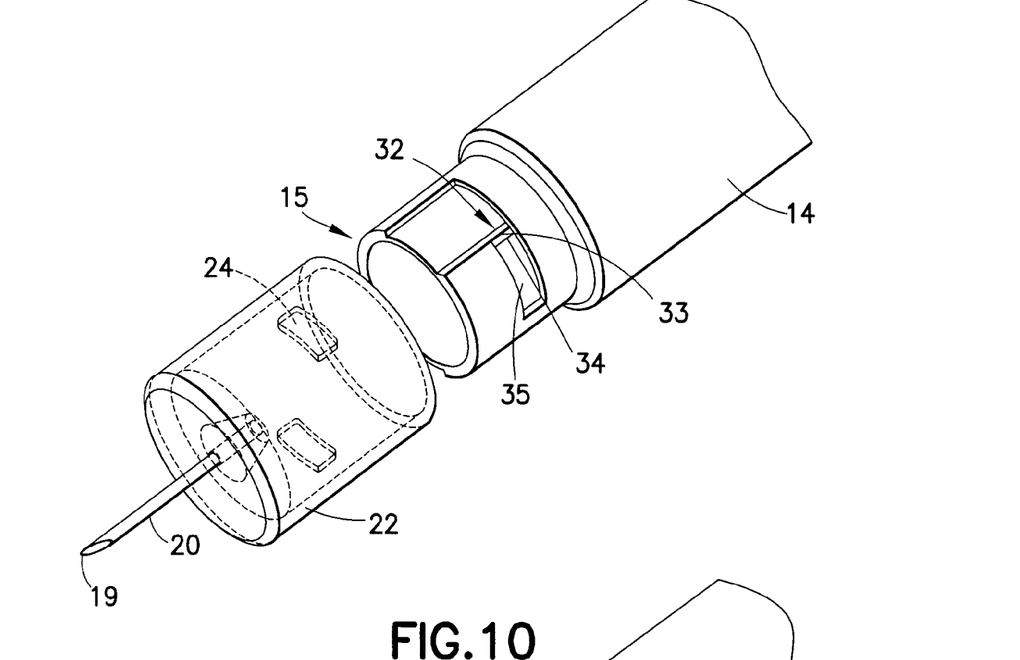
FIGS. 10-14 depict a pen needle assembly of the first embodiment of the present invention with various locking configurations.

With reference to FIGS. 10-14, the medical injector 10 may contain a locking configuration 32 for locking the pen needle assembly 12 to the injector body 14. The locking configuration 32 may be releasable or permanent depending on the medical injector. FIG. 10 shows a releasable lock 34 in the track 26 that enables the pen needle assembly 12 to be releasably locked to the injector body 14. The releasable lock 34 may include a ridge 33, preferably angled on both sides, creating a locking recess 35 in the second portion 30 of the track 26. Preferably, the ridge 33 is located at the juncture between the first portion 28 and the second portion 30 of the track 26. The ridge 33 is formed such that the guide key 24 can move over both sides of the ridge 33 in moving in and out of the locking recess 35. The ridge 33 provides an obstruction, and thus provides a locking effect to the guide key 24 moving out from the locking recess 35. With the hub 22 being of resilient material, deflection of the hub 22 permits the guide key 24 to traverse the ridge 33.

Figure 11:
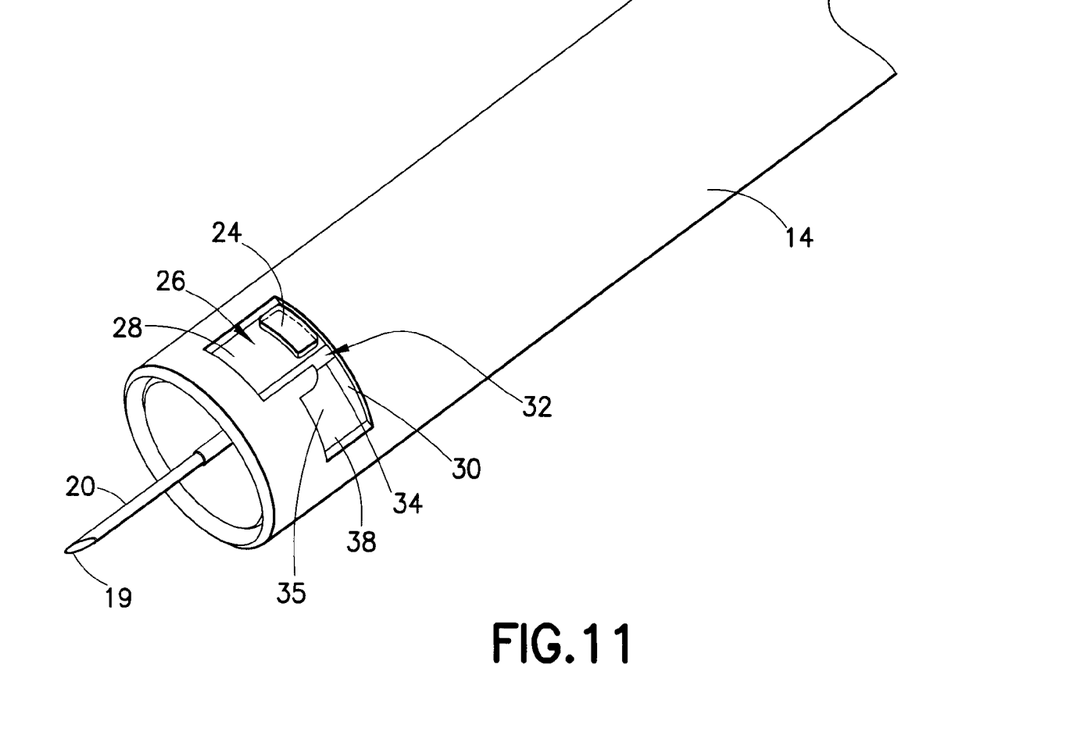
Figure 12:
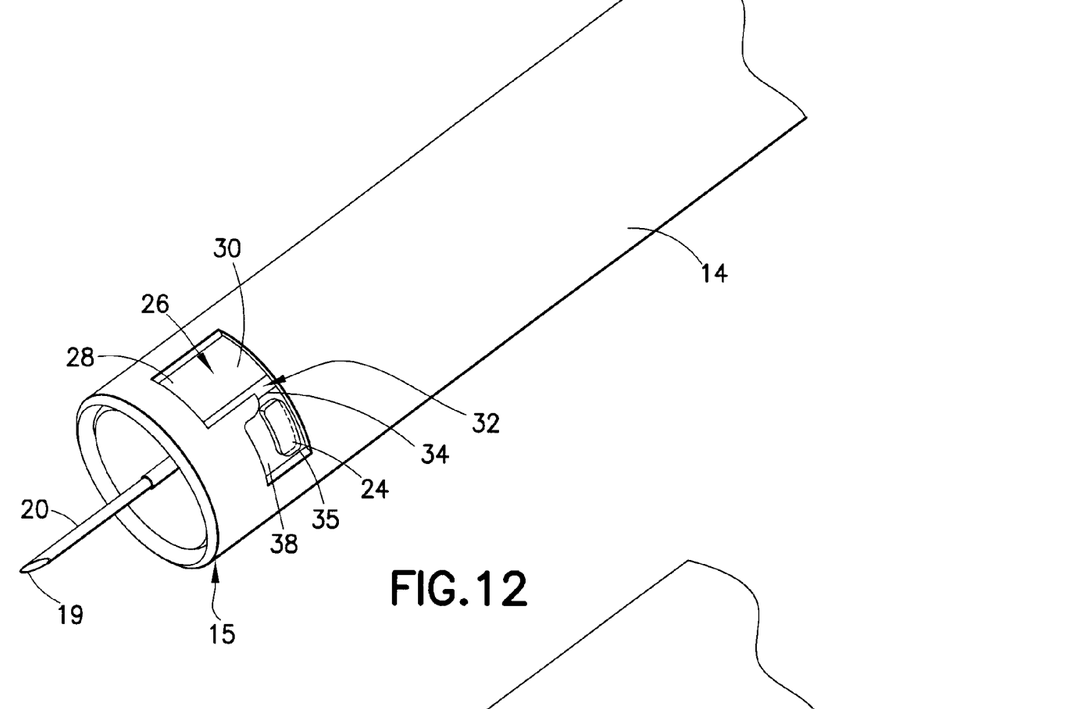
Figure 13:
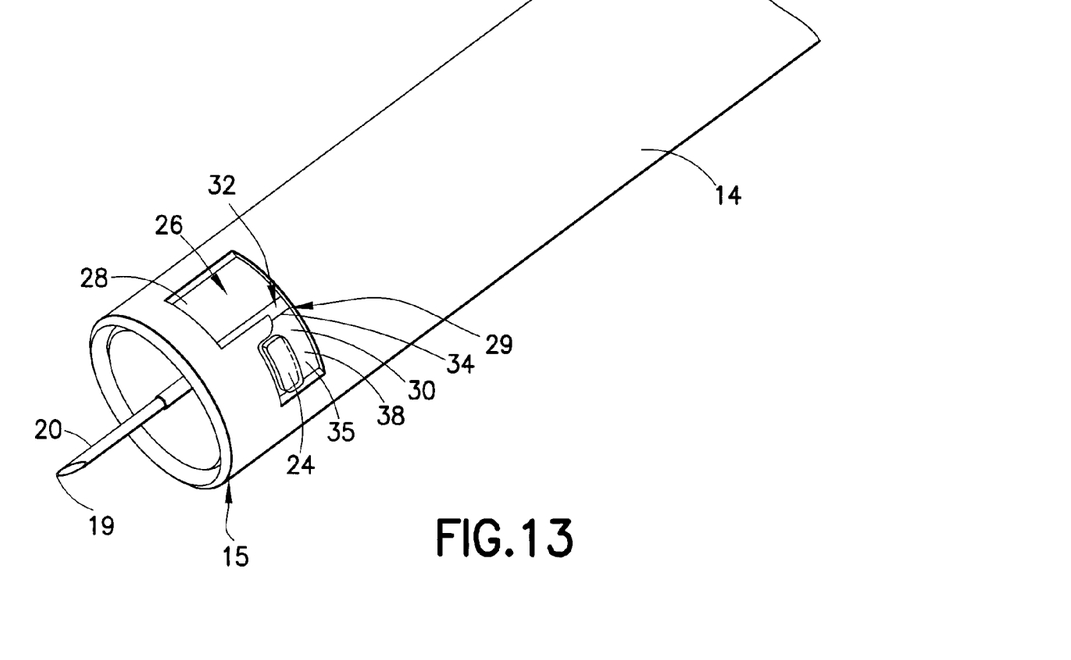

To further enhance the locking effect, as illustrated in FIGS. 11-13, the pen needle assembly 12 may be provided with an optional third portion 38 of the track 26. The third portion 38 of the track 26 traverses the second portion 30 of the track 26 and is designed to allow the needle 20 to move distally upon sufficient movement through the second portion 30. The third portion 38 is formed of limited length to ensure that the proximal end 21 of the needle 20 remains located proximally of the septum 18.

During use, after the guide key 24 is received by the first portion 28, as shown in FIG. 11, the pen needle assembly 12 is rotated along the second portion 30 of the track 26 until the releasable lock 34 is engaged, as shown in FIG. 12. To further enhance the locking effect, FIG. 13 shows the pen needle assembly 12 mounted with the guide key 24 in the optional third portion 38 of the track 26. A wall 29 is disposed between the first and third portions 28, 38 of the track 26 which prevents the guide key 24 from migrating to the first portion 26. The guide key 24 may be released from the third portion 38 by passage through the second portion 30 and traversal of the releasable lock 34. As will be appreciated by those skilled in the art, the third portion 38 may be used without the releasable lock 34 or other bodily arrangements.

Figure 14:
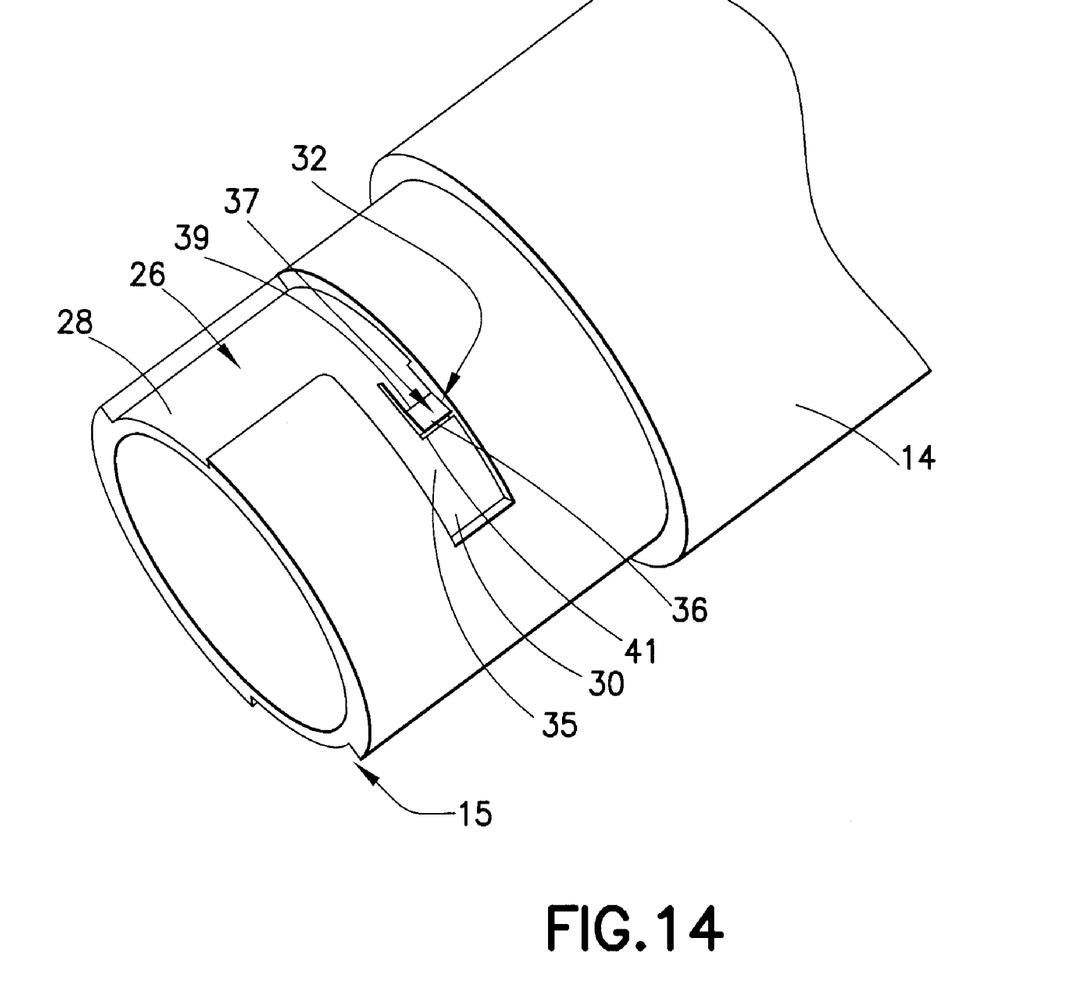

FIG. 14 provides a further embodiment of the present invention with a tab 37 used to form a permanent tab lock 36 instead of the releasable lock 34 used in FIG. 10. The permanent tab lock 36 includes a tab 37 with an angled side 39 and an adjacent side 41 that is generally perpendicular to the track 26, with a locking recess 35 being defined on the adjacent side of the tab 37. Such a design enables the guide key 24 to be guided over the angled side 39 of the tab 37 engaging the permanent tab lock 36, but prevents the guide key 24 from moving back over the adjacent side 41 after being locked into the locking recess 35.

The present invention also contemplates associating clicking noises with the locking configuration 32. More particularly, each releasable lock 34 or permanent tab lock 36 may create a clicking noise when engaged. Clicking noises with the locking configuration 32 may be a desirable feature because the clicking noise may provide assurance to the user that the pen needle 12 and injector body 14 are properly mounted and locked together. The clicking action may also provide tactile assurance of proper locking.

Figure 15:
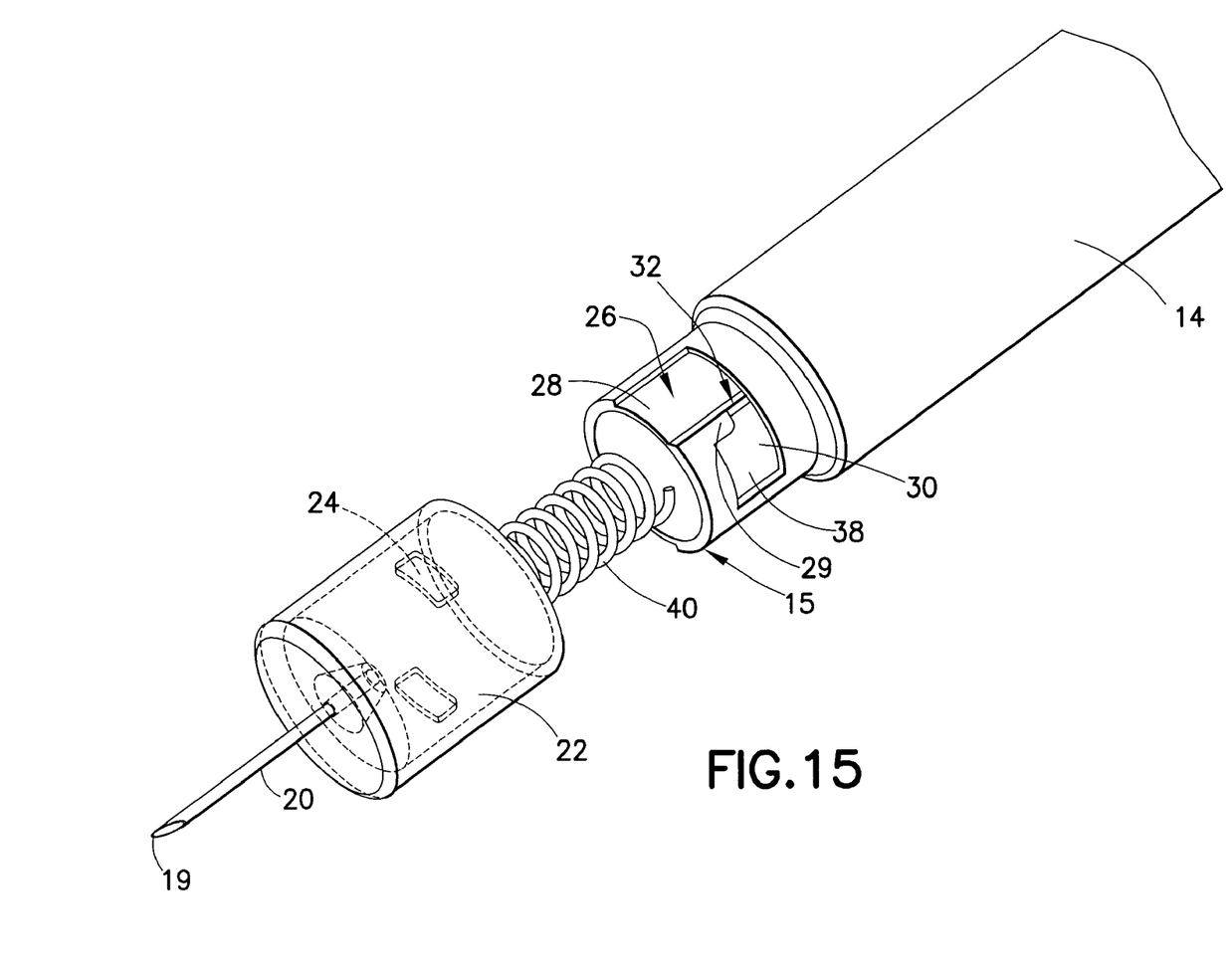
FIGS. 15-17 depict a pen needle assembly of a second embodiment of the present invention.

FIG. 15 shows a further embodiment of the medical injector 10 with an injector body 14 including a spring 40 and the third portion 38 of the track 26. This embodiment is similar to the arrangement shown in FIGS. 11-13. With the embodiment of FIGS. 11-13, manual movement is utilized to displace the guide key 24 in the third portion 38; and in this arrangement, the spring 40 provides a biasing force for urging the guide key 24 into the third portion 38. A locking arrangement (releasable or permanent) may be optionally utilized.

Figure 16:
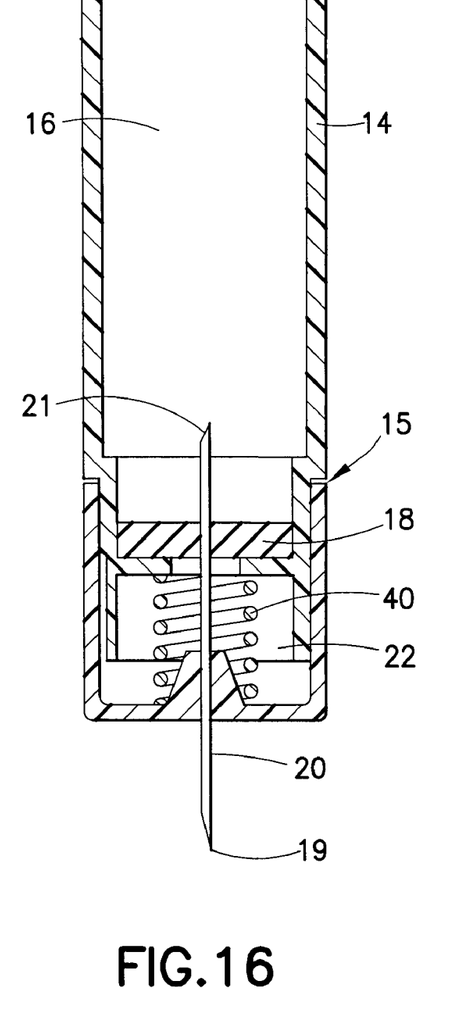
Figure 17:
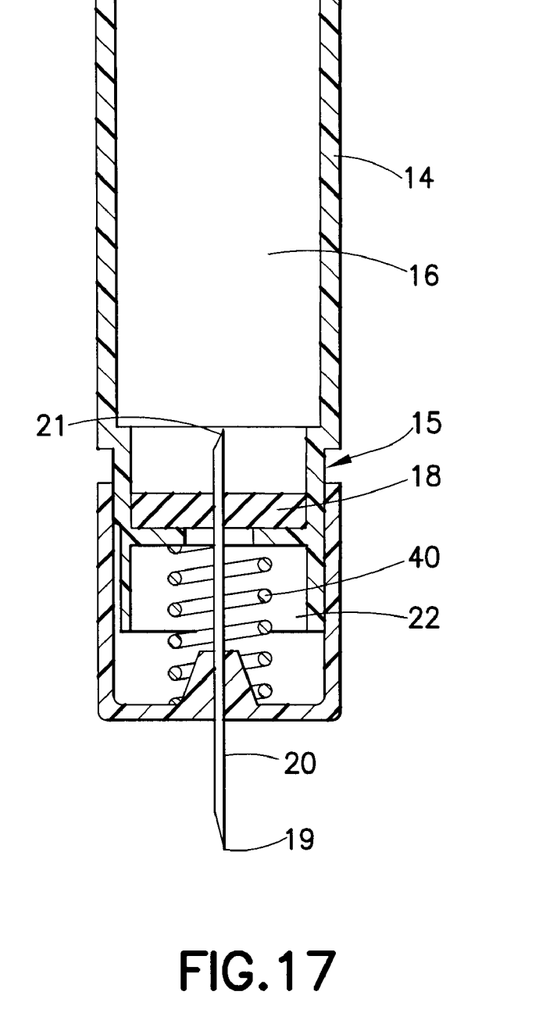

FIGS. 16-17 show partial cross-sectional views of the embodiment of FIG. 15 with the needle 20 in the second portion 30 of the track 26 (FIG. 16) and with the needle 20 in the third portion 38 of the track 26 (FIG. 17). The spring 40 causes the hub 22 to be displaced distally once the guide key 24 clears the wall 29, i.e., more sufficiently through the second portion 30. The spring 40 provides resistance against proximal movement of the hub 22 and, thus, enhances the locking effect applied to the hub 22.

The previous figures show the guide key 24 located on an inner portion of the hub 22. As shown in FIGS. 18-26, the guide key 24 may also be located on an outer portion of the hub 22. With the guide key 24 being on an outer portion of the hub 22, the injector body 14 may be formed to at least partially encase the hub 22.

Figure 18:
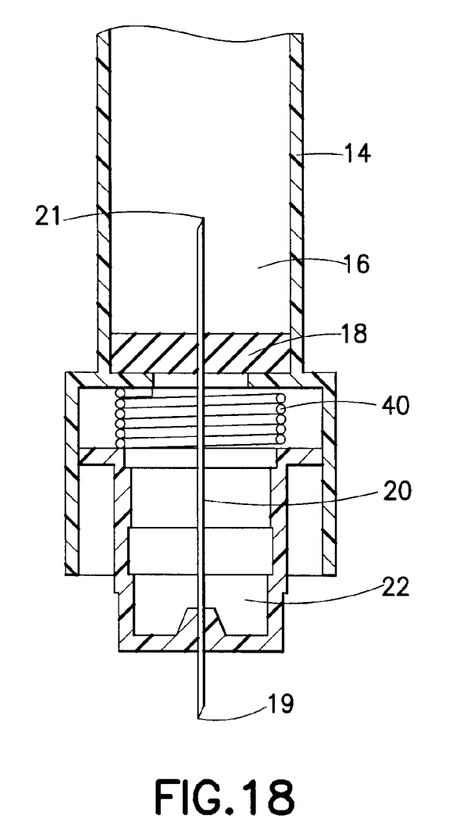
FIGS. 18-26 depict a variation of the second embodiment of the present invention with a guide key fixed to an outer portion of a hub.
Figure 19:
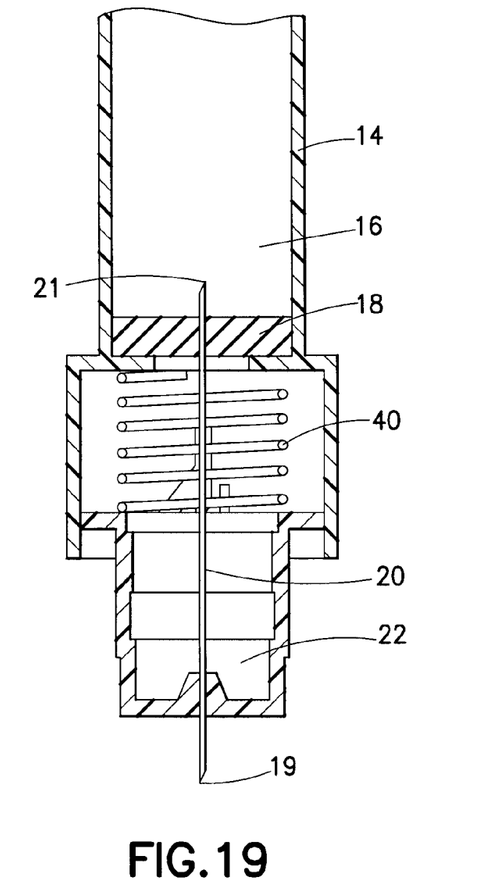

FIGS. 18-20 show an embodiment similar to that shown in FIGS. 15-17, except that the guide key 24 is located on the outer portion of the hub 22 and that the injector body 14 defines the track 26 exteriorly of the hub 22. More specifically, FIGS. 18-19 show partial cross-sectional views of the pen needle assembly 12 with the guide key 24 located on the outer portion of the hub 22. FIGS. 16 and 18 show the present invention after the proximal end 21 of the needle 20 fully pierces the septum 18 on the first portion 28 of the track 26. Afterwards the needle 20 is rotated and then moved distally along the third portion 38 of the track 26, with the proximal end 21 of the needle 20 remaining proximal to the septum 18, as shown in FIGS. 17 and 19.

FIGS. 20-25 show the pen needle assembly 12 of the present invention with the guide key 24 disposed on an outer portion of the hub 22 prior to being mounted onto the distal end 15 of the injector body 14. Here, the injector body 14 may be formed to have the track 26 defined externally and the guide key 24 may be located on the outer portion of the hub 22. The track 26 may be formed as a channel of limited depth, as shown in previous figures or be a through hole through the injector body 14, as shown in FIGS. 20-26. As one skilled in the art would appreciate, the track 26 may be configured using a combination of the arrangements provided herein.

Figure 21:
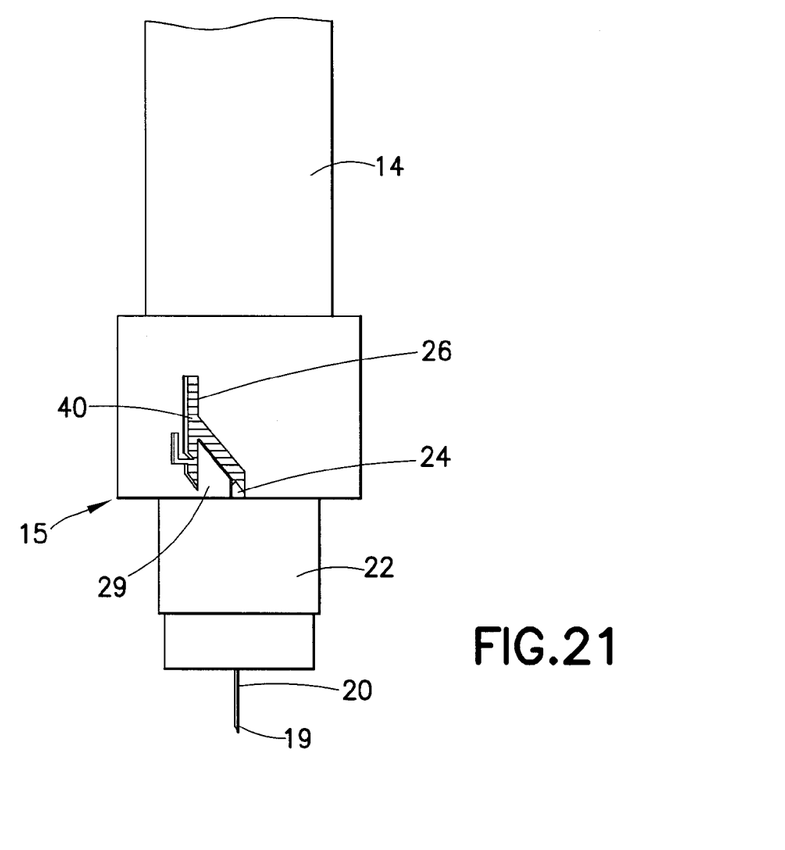
Figure 22:
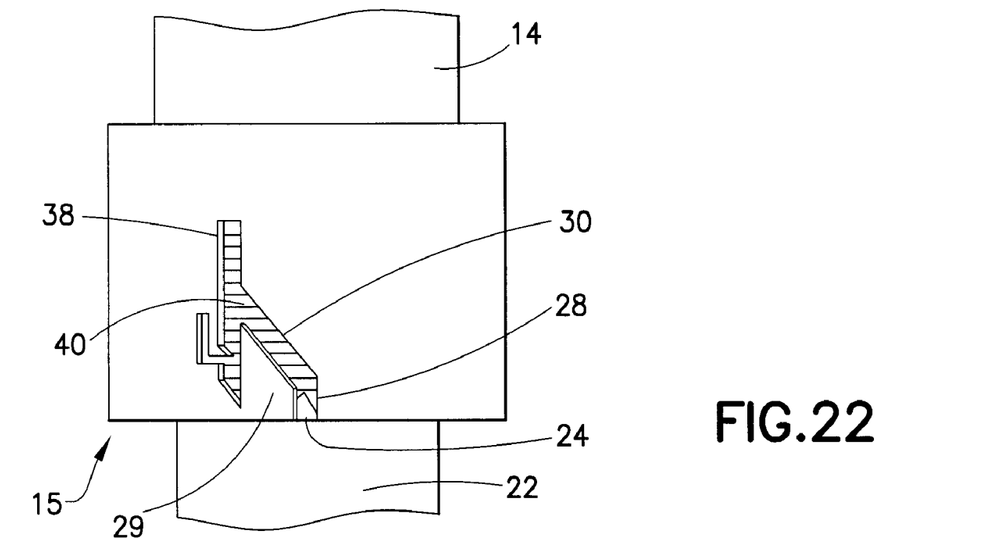
Figure 23:
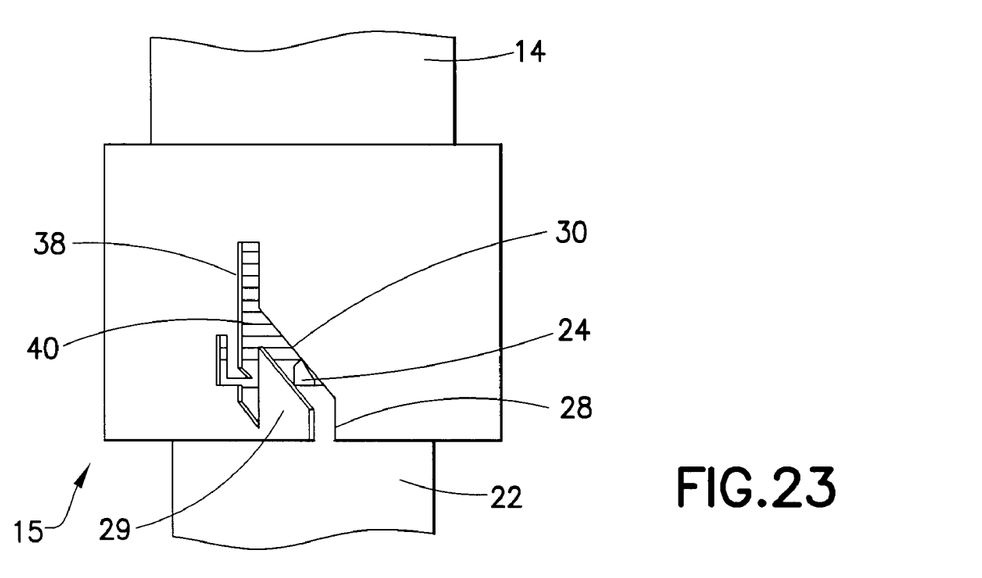
Figure 24:
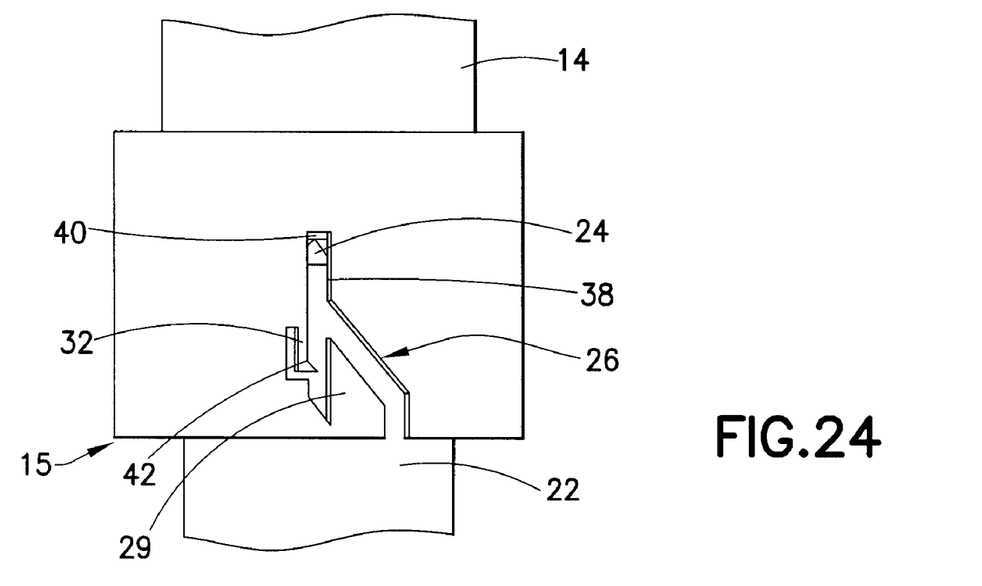
Figure 25:
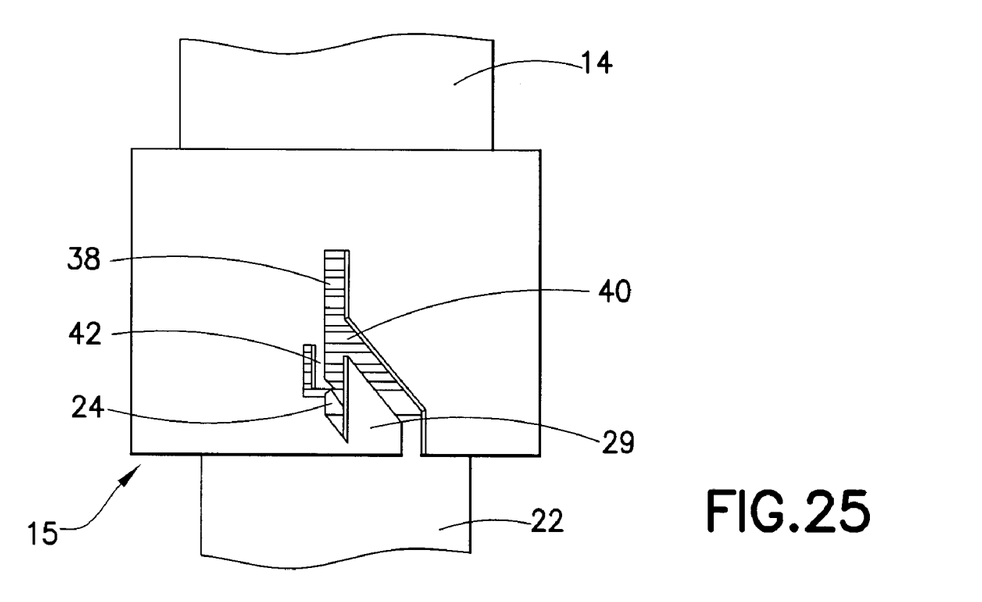

In FIGS. 21-22, the guide key 24 and the track 26 are aligned such that the first portion 28 of the track 26 receives the guide key 24. FIG. 23 shows the guide key 24 and track 26 after the pen needle assembly 12 is partially guided through the second portion 30 of the track 26. Then, in FIG. 24, the guide key 24 is in the third portion 38 of the track 26. Finally, FIG. 25 shows the guide key 24 in a locked position in the third portion 38 with the wall 29 separating the guide key 24 from the first portion 28. Optionally, the spring 40 may be utilized, as described above, to bias the pen needle assembly 12 distally.

As shown in the figures, the second portion 30 of the track 26 may be angularly disposed relative to the first portion 28 of the track 26. With the arrangement of FIG. 24, the second portion 30 of the track 26 is generally perpendicular to the first portion 28 of the track 26. As such, the guide key 24 is rotated after the guide key 24 sufficiently traverses the first portion 28 of the track 26 to reach the second portion 30 of the track 26. With the angled arrangement of FIG. 25, the guide key 24 is forced to rotate as it traverses the second portion 30 of the track 26. Therefore, the first portion 28 of the track 26 must be provided with sufficient length to ensure that the proximal end 21 of the needle 20 completely pierces the septum 18 before entering the second portion 30 of the track 26 and being rotated.

The second portion 30 may also be angularly disposed (perpendicular or at some other transverse position) to the third portion 38 of the track 26. In a preferred arrangement, the first portion 28 of the track 26 and the third portion 38 of the track 26 are generally parallel.

As shown in FIG. 25, various forms of the locking configurations 32 may be utilized. For example, a deflectable latch 42 may be utilized which is by-passed by the guide key 24 as traversing through the third portion 38 of the track 26. As appreciated by those skilled in the art, the latch 42 may be formed to be by-passed in both directions along the third portion 38 by the guide key 24 (i.e., in and out of the locking portion) in providing a releasable locking arrangement, or may be formed to be by-passed only in one direction (i.e., into the locking position) in providing a permanent one-time locking arrangement.

Figure 26:
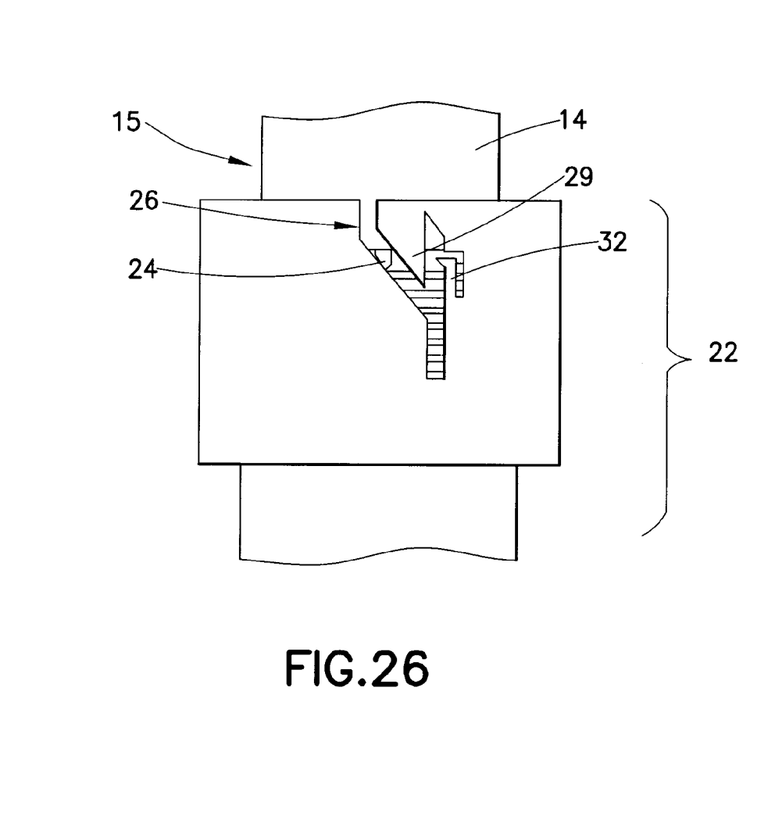

FIG. 26 provides a further feature of the present invention with the track 26 located on the hub 22, instead of the injector body 14, and the guide key 24 located on the injector body 14, instead of the hub 22. As one skilled in the art will appreciate, all configurations and features discussed above are useable with this arrangement. For example, an alternative configuration would allow the locking configuration 32 to include the track 26 and the locking recess 35 located on the hub 22 and the guide key 24 located on the injector body 14.

Figure 27:
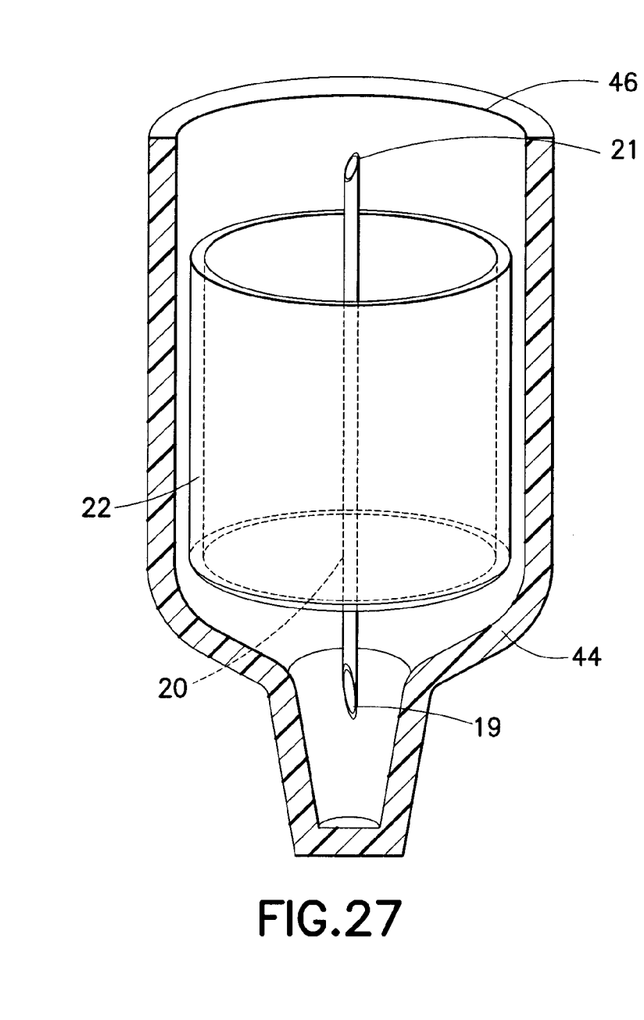
FIG. 27 depicts a pen needle assembly of the present invention with a cap surrounding the assembly.

With reference to FIG. 27, a cap 44 to accommodate the pen needle assembly 12 before and/or after use is shown. The cap 44 is designed to cover both the proximal and distal ends 19, 21 of the needle 20 in the pen needle assembly 12 and may be used with, but is not limited to the embodiments disclosed herein. The cap 44 is provided with an opening 46 for receiving the pen needle assembly 12. Before use, and to maintain an internal sterile environment, the opening 46 may be covered by a closure (not shown), which may be a rigid cap or flexible backing. The closure may be applied using standard techniques, such as a mechanical connector (e.g., threads, interference fit) or adherent connection.

What is claimed is:

1. A medical injector comprising:
a pen needle assembly including:
a hub; and
a needle fixed to said hub, said needle having a distal end, formed for insertion into a patient, and a proximal end;
an injector body being tubular in shape with a distal end and a proximal end;
a spring disposed between said injector body and said hub; and
a reservoir for medicament sealed by a septum, said reservoir being encased in said injector body;
wherein, a guide key is fixed to one of said hub or said injector body, a track being defined on the other of said hub or said injector body, said track having a first portion extending parallel to a longitudinal axis of said injector body, and a second portion disposed transversely to said first portion and a third portion disposed transversely to said second portion; and, wherein, said hub is formed to be telescopingly mounted onto said distal end of said injector body with said guide key being accommodated in said track, and wherein, with mounting said hub of said pen needle assembly onto said injector body, said first portion of said track being configured to receive said guide key and to guide said guide key in a straight line across sufficient distance to permit said proximal end of said needle to fully pierce through said septum without rotation of said needle, said proximal end of said needle being guided to a location proximal of said septum, and said second portion of said track being configured to permit said pen needle assembly to be turned with said guide key being received in said second portion of said track with said proximal end of said needle being located proximally of said septum, and
wherein, said spring being configured to bias said hub distally away from said injector body, said spring urging said guide key into said third portion of said track with said guide key being sufficiently moved through said second portion of said track.

2. A medical injector of claim 1, wherein said track is located on said hub.

3. A medical injector of claim 1, wherein said track is located on said injector body.

4. A medical injector of claim 3, wherein said first portion of said track extends proximally from said distal end of said injector body.

5. A medical injector of claim 1, wherein said second portion of said track is generally perpendicular to said first portion of said track.

6. A medical injector of claim 1, wherein said second portion of said track is generally non-perpendicular to said first portion of said track.

7. A medical injector of claim 1, wherein said first portion of said track and said third portion of said track are generally parallel.

8. A medical injector of claim 1, wherein said second portion of said track is disposed non-perpendicularly between said first portion of said track and said third portion of said track.

9. A medical injector of claim 1 further comprising a locking means for locking said guide key in said track.

10. A medical injector of claim 9, wherein said locking means includes at least one locking recess and said guide key is formed to be received and secured in said at least one locking recess.

11. A medical injector of claim 10, wherein said at least one locking recess is formed in said track of said hub and said guide key is formed on said injector body.

12. A medical injector of claim 10, wherein said at least one locking recess is formed in said track of said injector body and said guide key is formed on said hub.

13. A kit comprising:
the medical injector, as set forth in claim 1; and
a cap formed to accommodate said pen needle assembly.

* * * * *